United States Patent
Hörth et al.

(10) Patent No.: US 6,311,869 B1
(45) Date of Patent: Nov. 6, 2001

(54) APPARATUS FOR DISPENSING A MIXED MULTI-COMPONENT COMPOUND, IN PARTICULAR FOR DENTAL PURPOSES

(75) Inventors: Hans Hörth; Harald Pauls, both of Hamburg (DE)

(73) Assignee: Ernst Muhlbauer KG, Hamburg (DE)

( * ) Notice: Subject to any disclaimer, the term of this patent is extended or adjusted under 35 U.S.C. 154(b) by 0 days.

(21) Appl. No.: 09/669,309

(22) Filed: Sep. 25, 2000

(51) Int. Cl.$^7$ .............................. B67D 5/52; B65D 35/38
(52) U.S. Cl. .............................. 222/137; 222/567
(58) Field of Search ................. 222/137, 145.1, 222/325, 326, 327, 145.5, 153.09, 566, 567, 570

(56) References Cited

U.S. PATENT DOCUMENTS

| | | |
|---|---|---|
| Re. 34,487 | 12/1993 | Keller ................................. 222/137 |
| 4,767,026 | 8/1988 | Keller et al. ......................... 222/137 |
| 4,981,241 | 1/1991 | Keller ................................. 222/137 |
| 5,333,760 | 8/1994 | Simmen ............................... 222/137 |
| 5,924,600 | 7/1999 | Keller ................................. 222/137 |

*Primary Examiner*—Kevin Shaver
*Assistant Examiner*—Stephanie Wilatt
(74) *Attorney, Agent, or Firm*—Alix, Yale & Ristas, LLP

(57) ABSTRACT

Apparatus for dispensing a mixed multi-component compound, in particular for dental purposes. The adjacent outlet connection stubs of the component-containing containers bear a coupling plate on the end sides for the purpose of connecting a mixing nozzle. Said coupling plate forms a guide, running transversely to the direction of the outlet connection stubs, for a coupling slide with a coupling element which engages over a coupling flange provided on the mixing nozzle. The slide is in the form of a frame and is arranged permanently on the coupling plate.

9 Claims, 2 Drawing Sheets

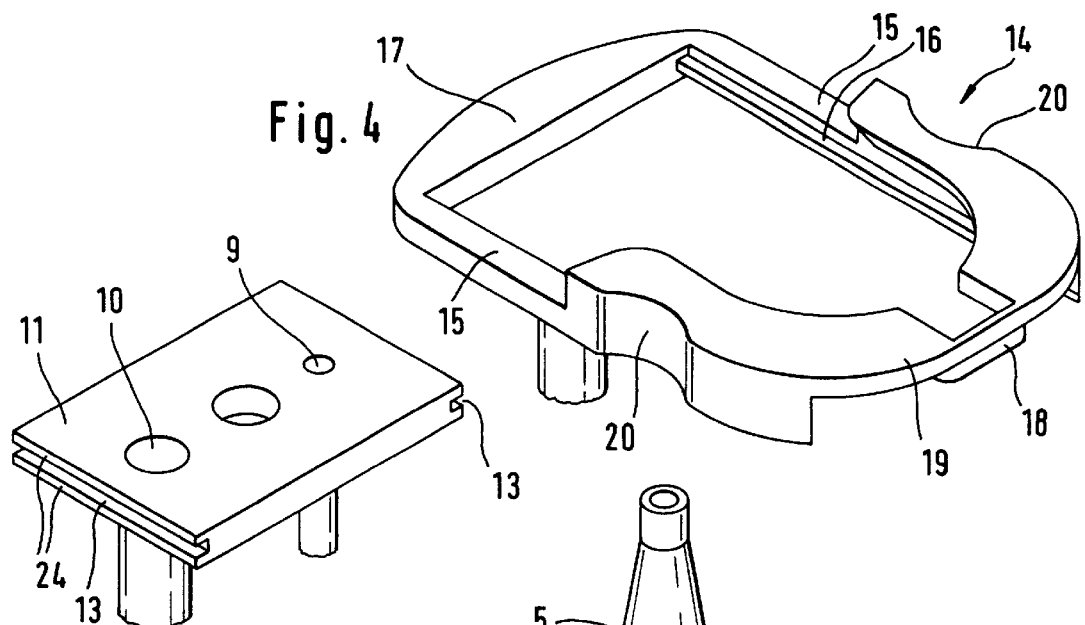
Fig. 4
Fig. 3
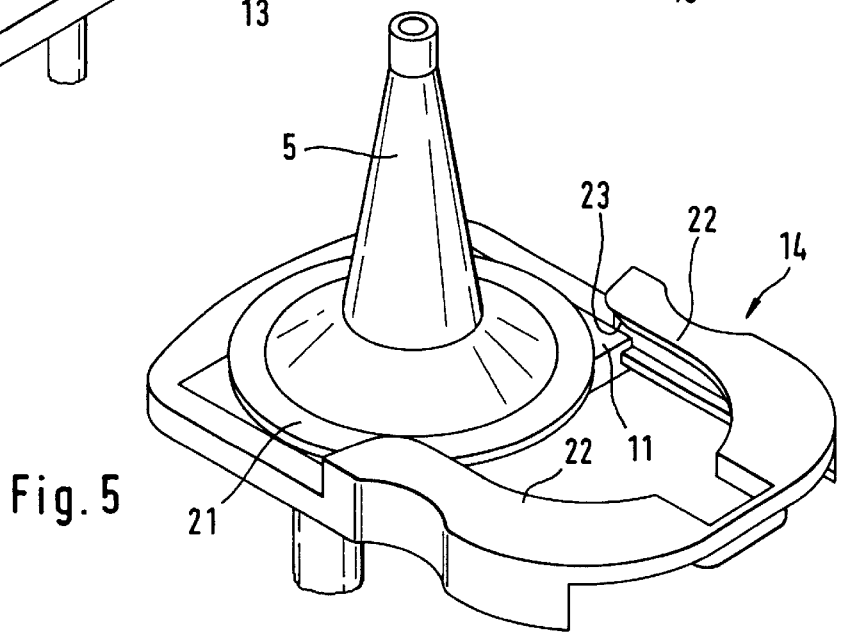
Fig. 5
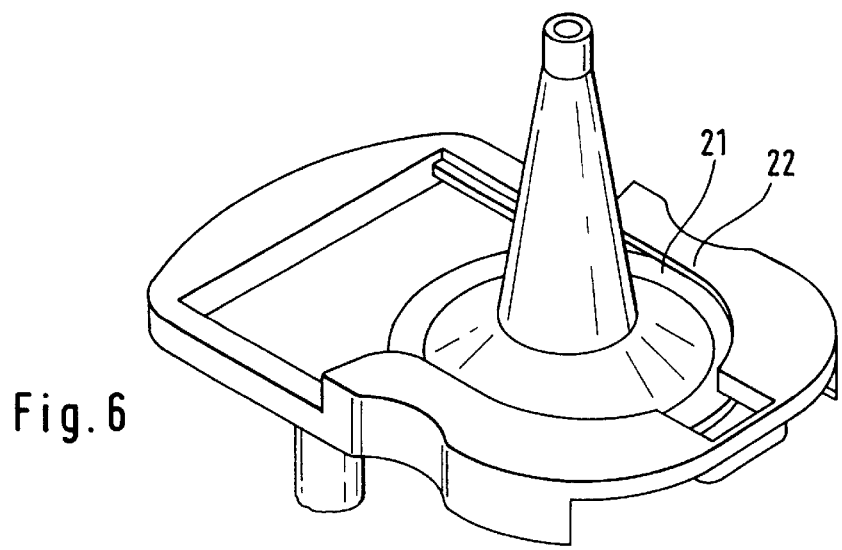
Fig. 6

APPARATUS FOR DISPENSING A MIXED MULTI-COMPONENT COMPOUND, IN PARTICULAR FOR DENTAL PURPOSES

BACKGROUND INVENTION

The invention relates to an apparatus for dispensing a mixed multi-component compound, in particular for dental purposes.

For producing multi-component dental impression compounds, use is made of units which are designed for accommodating a plurality of component-containing containers and for discharging the components from the containers. On the end side of the units, the containers have exposed outlet openings, to which the inlet openings of a mixing nozzle may be connected. The components come together in the mixing nozzle and leave the latter in the mixed state. Following the mixing operation, the compound hardens. This also applies to those components of the mixture which remain in the mixing nozzle once an impression-compound portion has been produced. Said mixing nozzle is configured such that the components only come together therein at a certain distance from the outlet openings of the cartridges, with the result that the hardening operation within the mixing nozzle remains restricted to a region sufficiently remote from the outlet openings of the containers. This makes it possible for a mixing nozzle which is used for producing an impression-compound portion and is rendered unusable by some of its contents hardening to be left on the unit in order to protect the outlet openings until the next portion is required. It is only then that the mixing nozzle is exchanged for a new one.

In a known unit disclosed in U.S. Pat. No. 5,333,760 the mixing nozzles are retained by a rotatable bayonet closure. A bayonet ring is retained on the mixing nozzle in an axially fixed but rotatable manner and, following the attachment of the nozzle to the outlet openings of the containers, is rotated in order to come into positively locking engagement with a pair of claws on the end side of the containers. The ring involves high outlay in terms of its connection to the mixing nozzle and because a comparatively large number thereof is required, specifically one for each mixing nozzle. This applies correspondingly to another known arrangement (EP-A-730 913), in which the bayonet coupling elements are arranged on the mixing-nozzle housing, which contains, in a rotatable manner relative to the housing, an insert which forms the inlet opening of the mixing nozzle. A design (DE-U-298 20 831) in which a locking means is arranged on the unit for the purpose of retaining the mixing nozzle involves less outlay. This means that it is not necessary for each individual mixing nozzle to be equipped with a bayonet element. However, it has been found that this design does not afford sufficient stability.

The apparatus according to FIG. 4 from U.S. Pat. No. 4,753,536 comprises two component-containing containers which are fixed to one another and bear outlet connection stubs adjacent to one another on the end sides. It is possible to fit onto the outlet connection stubs a mixing nozzle which can be secured in the fitted position by a coupling device. The coupling device comprises a coupling plate which is borne by the outlet connection stubs and forms a guide, running transversely to the direction of the outlet connection stubs, for two coupling slides. The latter can be displaced into a closed position on the guide in opposite directions and bear coupling strips which, in the closed position, engage over a coupling flange of the mixing nozzle through 180° in each case.

SUMMARY OF THE INVENTION

The object of the invention is to provide an apparatus of the type mentioned in the introduction which has improved handling.

For this purpose, provision is made for the coupling slide to be in the form of a frame, and for displacement from the closed position into an open position, in which the coupling strips are free of the coupling flange, to be limited by contact with the coupling slide on a frame side.

The actuation of one coupling slide means reduced outlay in comparison with the actuation of two coupling slides, as in U.S. Pat. No. 4,753,536. Contact with the coupling slide on a frame side provides a defined open position, which allows the mixing nozzle to be attached to the outlet connection stubs and also allows the removal of the mixing nozzle. In the open position, the coupling slide remains on the unit and does not have to be attached laboriously again for a renewed closing operation. Considerably easier handling is achieved overall.

On its side which is directed towards the plate, the mixing nozzle is preferably bounded by a surface which rests over a large surface area on the surface of the plate.

Since the coupling plate is arranged directly on the containers and/or the connection stubs thereof, positional tolerances between the containers and the unit do not affect the securing of the mixing nozzle. Rather, the coupling forces are transmitted over an extremely short distance from the mixing nozzle to the outlet connection stubs. This makes it possible for the relevant components to be of less rigid design, consequently involving less outlay, than if the force transmission were to extend over a larger distance.

In the closed position, the coupling slide grips, by means of its coupling elements, the coupling flange of the mixing nozzle in such a way that the mixing nozzle is retained in sufficiently firm and sealed abutment against the outlet connection stubs and/or the coupling plate. Said coupling flange is gripped at least at two points which are offset by 180° in relation to one another. The coupling action expediently covers an angle of at least 180°, with the result that the coupling flange does not lack support over more than 180°. If a plurality of grip points are provided, these are spaced apart from one another by not more than 180°. If a single coupling element, which covers the border of the coupling flange continuously, is provided, this has to extend over at least 180° . If a plurality of coupling elements are provided, this is not necessary.

In one embodiment of the invention, the guide for the coupling slide is formed by two parallel strips on the coupling plate and two strips, engaging behind the same, of the coupling slide. The latter can thus be displaced in a translatory manner transversely to the direction of the outlet connection stubs. The guide strips are expediently continuous. Of course, however, it is also possible for in each case one of these to be made up of a plurality of spaced-apart protrusions. The slide has coupling strips in its region which interacts with the coupling flange of the mixing nozzle in the closed position. If, following the attachment of the mixing nozzle, the slide is pushed into its closed position, then the coupling strips are pushed over that part of the mixing-nozzle coupling flange which is adjacent to them in each case and thereby prevent the mixing nozzle from moving away from the coupling plate. As a result, the mixing nozzle is secured in the coupled position.

In a further embodiment, the coupling plate and the coupling flange have corresponding and adjacent coupling borders, and there is provided a coupling slide which can be pushed over the two borders, from the side, in order to enclose the same in the closed position of said coupling slide.

BRIEF DESCRIPTION OF THE DRAWINGS

The invention is explained in more detail hereinbelow with reference to the drawing, which illustrates advantageous exemplary embodiments and in which:

FIG. 3 shows an embodiment of the coupling plate on an enlarged scale,

FIG. 4 shows the slide belonging to the coupling plate according to FIG. 3, and

FIGS. 5 and 6 show the combination of the coupling plate, of the slide and of the mixing nozzle in different functional positions.

DETAILED DESCRIPTION OF THE PREFERRED EMBODIMENTS

The unit 1 contains a mount 2 and an emptying drive for two containers 3, 4 which contain the components of a dental impression compound. The components are discharged by way of a mixing nozzle 5, from which said components emerge as a mixed, ready-to-use tooth-impression compound.

Figure 1:
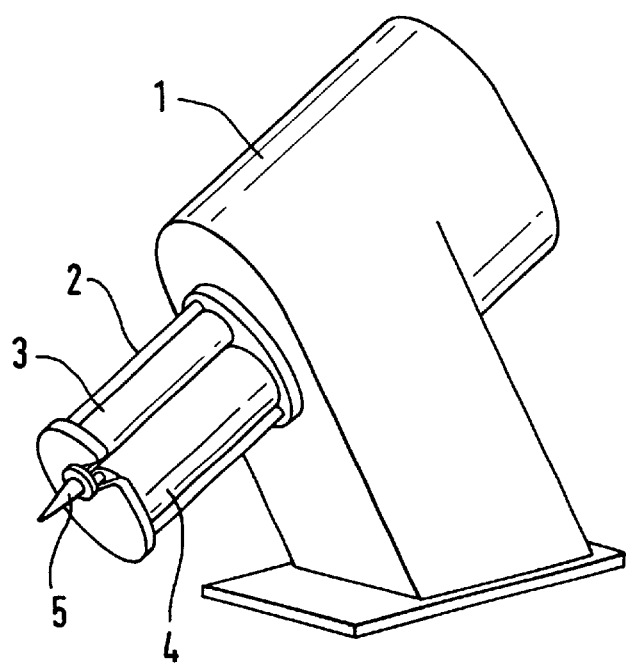
FIG. 1 shows a view of the unit in its entirety.
Figure 2:
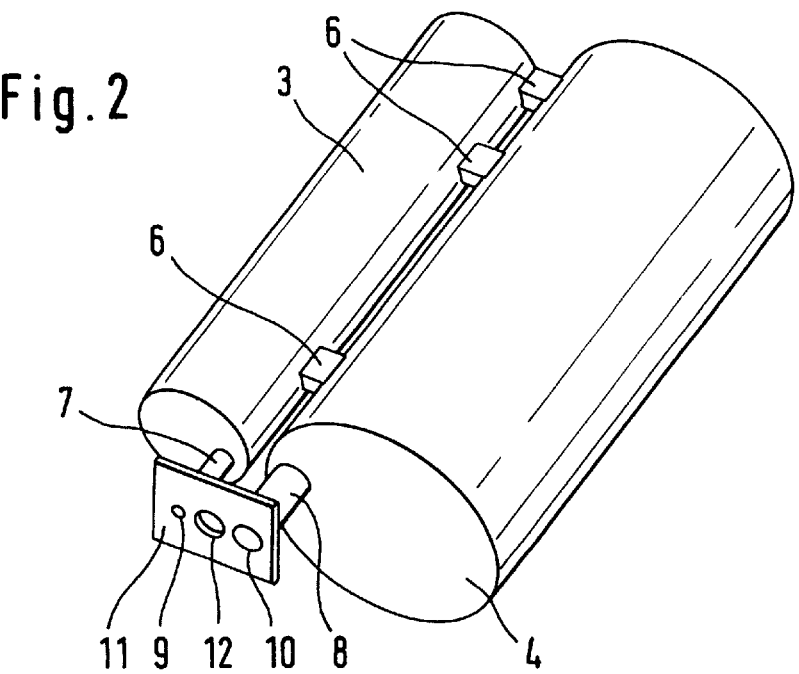
FIG. 2 shows a pair of containers connected to one another.

As can be seen in FIG. 2, the containers 3, 4 are fixed to one another via suitable material bridges 6. Each container 3, 4 has a respective outlet connection stub 7, 8, which opens out in an outlet opening 9, 10, respectively. These openings are located in a coupling plate 11, which is fixed to the outlet connection stubs 7, 8. It would also be sufficient if said coupling plate were connected to just one outlet connection stub, provided that the latter is sufficiently strong and rigid in order also to ensure the desired position of the coupling plate 11 in relation to the other outlet connection stub. The coupling plate 11 contains a central opening 12 through which a drive shaft for driving the mixer shaft of a dynamic mixer may be routed if desired. Since this is known, it will not be explained in any more detail here.

As can be seen in FIG. 3, the coupling plate 11, on two opposite, parallel sides, has guide grooves 13 between guide strips 24, which run parallel to one another and to the plane of the coupling plate 11. They serve for the guidance connection to the slide 14 (FIG. 4). The latter is in the form of a frame. Two frame sides 15 each bear a guide strip 16 on their mutually facing inner sides. The dimensions and spacings of the guide strips 16 match the guide grooves 13 of the guide plate 11. The slide can be pushed onto the guide plate 11 with its side which appears on the right in the drawing in front. Its allowance for movement in relation to the guide plate 11 is then given by its third frame side 17 and a stop 18 on the fourth frame side 19. The stop 18 is designed such that it can yield elastically when the slide is pushed onto the coupling plate 11, but prevents the undesired action of the slide sliding off the coupling plate 11. The coupling slide 14 is expediently provided with grip hollows 20 or the like for easier displacement in relation to the coupling plate 11.

FIG. 5 illustrates the slide 14 fitted on the coupling plate 11, to be precise in the open position of the slide, in which the mixing nozzle 5 can be fitted onto the coupling plate 11 and removed therefrom. The inlet openings of the mixing nozzle are designed in relation to the outlet openings 9, 10 in the coupling plate such that there is a sealed connection when the coupling flange 21 of the mixing nozzle butts against the surface of the coupling plate 11.

In that part of the slide which is on the right (in the drawing), the frame parts 15 are provided with coupling strips 22 which, when the slide is pushed into its closed position (FIG. 6), engage over those border regions of the coupling flange 21 which are adjacent to them. The distance between the underside of the coupling strips 22 and the surface of the coupling plate 11 is selected such that the coupling flange 21 is retained firmly on the coupling plate 11. In order that the slide 14 can easily be pushed from the open position into the closed position, the undersides of the coupling strips 22 are bevelled slightly at the opening end 23 of the same.

What is claimed is:

1. Apparatus for dispensing a mixed multi-component compound, in particular for dental purposes, comprising:

a plurality of component-containing containers having end sides and which are fixed to one another and have respective outlet connection stubs adjacent to one another on the respective end sides and which extend in a common direction;

means for mounting said first and second containers;

means for discharging the components from the containers;

a mixing nozzle, said mixing nozzle including means for defining communication with the outlet connection stubs of the containers and a coupling flange;

a coupling plate which is borne by at least one of the outlet connection stubs and forms a guide transverse to the direction of the outlet connection stubs; and a frame shaped coupling slide, which can be displaced between open and closed positions, said frame shaped coupling slide in said closed position having at least one coupling element which engages over the coupling flange of the mixing nozzle at least on two opposite sides thereof, said frame shaped coupling slide in said open position being disengaged from the coupling flange.

2. The apparatus in accordance with claim 1, wherein said means for defining communication with the outlet connection stubs of the containers includes means cooperating with said coupling plate.

3. The apparatus in accordance with claim 2, wherein the guide for the coupling slide is formed by two sets of two parallel strips on the coupling plate that define first and second grooves on opposed surfaces of the coupling plate and first and second strips on opposed surfaces of the coupling slide that are dimensioned and configured for sliding engagement with respectively said first and second grooves.

4. Apparatus for dispensing a mixed multi-component compound, in particular for dental purposes, which comprises:

first and second containers dimensioned and configured for respectively holding first and second components, said first and second containers having respective first and second outlet connection stubs;

means for mounting said first and second containers;

means for discharging the contents of said first and second containers;

a mixing nozzle, said mixing nozzle having a coupling flange;

means for providing communication between said mixing nozzle and said first and second outlet connection stubs, said means for providing communication including a coupling plate, said coupling plate being disposed in generally transverse relationship to said first and second outlet connection stubs and having guide means disposed on opposed surfaces;

means for supporting said coupling plate; and a coupling slide, said coupling slide including means for engaging said coupling flange and said opposed surfaces of said coupling plate, said coupling slide being movable between an open position and a closed position, said coupling slide in said closed position locking said coupling flange of said mixing nozzle in communication with said first and second outlet connection stubs, said coupling slide in said open position allowing replacement of said mixing nozzle.

5. Apparatus for dispensing a mixed multi-component compound, in particular for dental purposes, comprising:

a plurality of component-containing containers having end sides and which are fixed to one another and have respective outlet connection stubs adjacent to one another on the respective end sides and which extend in a common direction;

a support dimensioned and configured for mounting said first and second containers;

a mixing nozzle having a coupling flange;

a coupling plate which is supported by at least one of the outlet connection stubs and has at least one guide surface transverse to the direction of the outlet connection stubs, the coupling plate being in communication with the outlet connection stubs; and a frame shaped coupling slide meshing with said at least one guide surface of said coupling plate for sliding movement, the sliding movement allowing displacement between open and closed positions, said frame shaped coupling slide in said closed position having at least one coupling element which engages over the coupling flange of the mixing nozzle at least on two opposite sides thereof to provide communication between the outlet connection stubs with the mixing nozzle via said coupling plate, said frame shaped coupling slide in said open position being disengaged from the coupling flange of the mixing nozzle.

6. The apparatus in accordance with claim 5, wherein the at least one guide surface comprises a first set of two parallel strips on the coupling plate that define first and second grooves on one surface of the coupling plate.

7. The apparatus in accordance with claim 6, wherein at least one guide surface includes a second set of two parallel strips on the coupling plate that define first and second grooves on a second surface of the coupling plate.

8. The apparatus in accordance with claim 7, wherein the first and second sets of two parallel strips are on opposed sides of the coupling plate.

9. The apparatus in accordance with claim 8, wherein the frame shaped coupling slide is dimensioned and configured for sliding engagement with the first and second grooves on opposed surfaces of the coupling plate.

* * * * *

UNITED STATES PATENT AND TRADEMARK OFFICE
CERTIFICATE OF CORRECTION

PATENT NO.    : 6,311,869 B1
DATED         : November 6, 2001
INVENTOR(S)   : Horth et al.

It is certified that error appears in the above-identified patent and that said Letters Patent is hereby corrected as shown below:

<u>Title page,</u>
After item "[22] Filed: Sep. 25, 2000" insert
-- [30] Foreign Application Priority Data
Sep. 27, 1999 (DE) . . . . . . . . . 299 17 013.6 --

Signed and Sealed this

Thirteenth Day of August, 2002

*Attest:*

*Attesting Officer*

JAMES E. ROGAN
*Director of the United States Patent and Trademark Office*